United States Patent [19]

John et al.

[11] Patent Number: 5,324,436
[45] Date of Patent: Jun. 28, 1994

[54] USE OF HYDRATE FORMATION TO CONTROL MEMBRANE MIMETIC SYSTEMS

[75] Inventors: Vijay T. John, Kenner, La.; Joseph A. Akkara, Holliston; David L. Kaplan, Stow, both of Mass.

[73] Assignee: The Administrators of the Tulane Educational Fund, New Orleans, La.

[21] Appl. No.: 31,168

[22] Filed: Mar. 12, 1993

Related U.S. Application Data

[63] Continuation-in-part of Ser. No. 806,553, Dec. 13, 1991, abandoned.

[51] Int. Cl.$^5$ ............................................. B01D 61/32
[52] U.S. Cl. .................................... 210/638; 210/643
[58] Field of Search ...................... 210/638, 643, 632

[56] References Cited

U.S. PATENT DOCUMENTS 4,438,052  3/1984  Weder et al. ...................... 264/4.6
4,678,583  7/1987  Willson, III et al. ............... 210/638

OTHER PUBLICATIONS

Barbaric et al., "Micellar Solubilization of Biopolymers in Organic Solvents. 5. Activity and Conformation of α-Chymotrypsin in Isooctane-AOT Reverse Micelles," *J. Am. Chem. Soc.*, vol. 103, pp. 4239–4244 (1981).
Candau et al., "Inverse Microlatexes: Mechanism of Formation and Characterization," *Structure and Reactivity in Reverse Micelles*, pp. 361–370 (M. P. Pileni, ed. 1989).
Hagen et al., "Protein Refolding in Reversed Micelles," *Biotechnology and Bioengineering*, vol. 35, pp. 955–965 (1990).
John et al., "Pressurized Gases in Contact with Liquid Reversed Micellar Solutions: Effects on Micellar Size and Stability, Biotechnological Application," *Proceedings of the Second International Symposium on Supercritical Fluids*, pp. 70–73 (1991).
Kabanov et al., "Enzymes Entrapped in Reversed Micelles of Surfactants in Organic Solvents: A Theoretical Treatment of the Catalytic Activity Regulation", *J. Theor. Biol.*, vol. 133 pp. 327–343 (1988).
Kortan et al., "Nucleation and Growth of CdSe on ZnS Quantum Crystallite Seeds, and Vice Versa, in Inverse Micelle Media," *J. Am. Chem. Soc.*, vol. 112, pp. 1327–1332 (1990).
Luisi, P. L., "Enzymes Hosted in Reverse Micelles in Hydrocarbon Solution," *Angewandte Chemie International Edition in English*, vol. 24, pp. 439–450 (1985).
Nguyen et al., "Characteristics of Protein-Containing Reversed Micelles Subjected to Hydrate Formation Conditions," *J. Phys. Chem.* vol. 95, pp. 1467–1471 (1991).
Nguyen et al., "Clathrate Hydrate Formation in Reversed Micelles," *J. Phys. Chem.*, vol. 93, pp. 8123–8126 (1989).
Phillips et al., "Protein Recovery from Reversed Micellar Solutions through Contact with a Pressurized Gas Phase," *Biotechnology Progress*, vol. 7, pp. 43–48 (1991).
Rao et al., "Modification of Enzyme Activity in Reversed Micelles through Clathrate Hydrate Formation," *Biotechnology Progress*, vol. 6, pp. 465–471 (1990).
Zulauf et al., "Inverted Micelles and Microemulsions in Ternary System $H_2O$/Aerosol-OT/Isooctane As Studied by Photon Correlation Spectroscopy," *J. Phys. Chem.*, vol. 83, pp. 480–486, (1979).
Akkara et al., "Synthesis and Characterization of Polymers Produced by Horseradish Peroxidase in Dioxane," *J. Polymer Sci.*, vol. 29, pp. 1561–1574 (1991).
Dordick et al., "Polymerization of Phenols Catalyzed by Peroxidase in Nonaqueous Media," *Biotechnol. Bioeng.*, vol. 30, pp. 31–36 (1987).

*Primary Examiner*—Frank Spear
*Attorney, Agent, or Firm*—Olson & Hierl, Ltd.

[57] ABSTRACT

A process is disclosed for regulating the size and composition of the internal reaction medium of a membrane mimetic system using clathrate hydrate formation under gas pressure conditions. When the disclosed membrane mimetic system is in contact with a clathrate forming gas, some of the water in the internal reaction medium is converted to crystalline hydrate form, which physically and chemically isolates the water from the remainder of the internal reaction medium. In one preferred process embodiment, the membrane mimetic system is used for enzymatic polymer synthesis in an organized medium to control the size and morphology of the polymer particles formed.

26 Claims, 7 Drawing Sheets

USE OF HYDRATE FORMATION TO CONTROL MEMBRANE MIMETIC SYSTEMS

This invention was made with United States Government support under Control Number DAAK6091-C-0119 awarded by the U.S. Army Natick Research, Development and Engineering Center. The United States Government has certain rights in the invention.

CROSS REFERENCE TO RELATED APPLICATION

This is a continuation-in-part of co-pending application Ser. No. 806,553 filed on Dec. 13, 1991, now abandoned.

TECHNICAL FIELD

The present invention relates generally to the field of biotechnology and more specifically to methods for controlling reactions within the internal reaction medium of a membrane mimetic system using hydrate formation.

BACKGROUND OF THE INVENTION

Water-in-oil microemulsions, also known as reversed micelies, are being used in increasing number of commercial and industrial applications. They are of interest due to their physicochemical characteristics particularly relevant to biomembrane mimetic phenomena, protein extraction processes, and biocatalysis in minimal water systems. The uses include such diverse fields as bioseparations, polymerization and particle synthesis. Depending on the uses and the intended applications, the reversed micelles may be prepared by the methods well known to those skilled in the art.

Conventional processes use reversed micelles as they exist in solution. Potential application of reversed micelles is limited by the original size and composition of the internal reaction media. It is desirable to control these factors in situ so that the reaction media itself and the products formed thereby can be controlled.

SUMMARY OF THE INVENTION

The present invention is directed to a process for regulating the size and composition of the internal reaction medium of a membrane mimetic system through clathrate hydrate formation and to enzymatic polymer synthesis in an organized medium.

When a membrane mimetic system is contacted with clathrate forming gas such as methane and pressurized, some of the water in the internal reaction medium is converted to a crystalline hydrate form. This physically and chemically isolates the water from the remainder of the internal reaction medium. The water content of the membrane mimetic system is thereby reduced and the membrane system shrinks in size. By adjusting the pressure the system is exposed to, the amount of water that drops out of the membrane solution can be controlled; thus the size and composition of the internal solution of the membrane mimetic system can be precisely controlled by adding or removing gas from the system. The hydrate formation process is totally reversible by manipulating the gas pressure within the system.

According to the present invention, a reaction medium enclosed in a membrane mimetic system is admixed as a solution containing a solvent and a solute. The initial concentration of the solute in the solution is insufficient to change the reaction mechanism of the solution. A portion of the solvent in the solution is then reversibly isolated so that the effective concentration of the solute in the solution is raised to a level sufficient to change the reaction medium mechanism. The isolated portion of the solvent is then released, thereby reducing the effective concentration of the solute in the solution.

In a preferred embodiment, a gas such as methane is used to form a clathrate hydrate to isolate the portion of the solvent which, in this embodiment, is water. The resulting increase in solute concentration changes the reaction medium mechanism.

According to the present invention, the reaction medium admixture is pressurized with a gas which reversibly combines with a portion of the solvent to form a clathrate hydrate so as to raise the effective concentration of the solute in the admixture to a level sufficient to cause the desired changes in the reaction medium mechanism. The isolated portion of the solvent is released into solution by reducing the pressure of the gas to melt the clathrate hydrate. The reaction medium mechanism changes as the concentration of the solute changes.

A distinctive feature of this invention is that the reaction medium can be repeatedly controlled in situ.

In another preferred embodiment, the disclosed membrane mimetic system is used as an organized medium for enzymatic polymer synthesis to control the size and morphology of the polymer particles formed.

The present invention provides for improved control and reproducibility over the reaction medium through adjustment of the pressure and temperature of the solution. The cost and effectiveness of the control is also enhanced.

Contamination of a protein solute is prevented by eliminating the addition of other compounds to the reaction medium solution to control the reactions therein.

Other and further advantages, embodiments, variations and the like will be apparent to those skilled in the art from the present specification taken with the accompanying drawings and appended claims.

BRIEF DESCRIPTION OF THE DRAWINGS

In the drawings, which comprise a portion of this disclosure.

DESCRIPTION OF THE PREFERRED EMBODIMENTS

Figure 1:
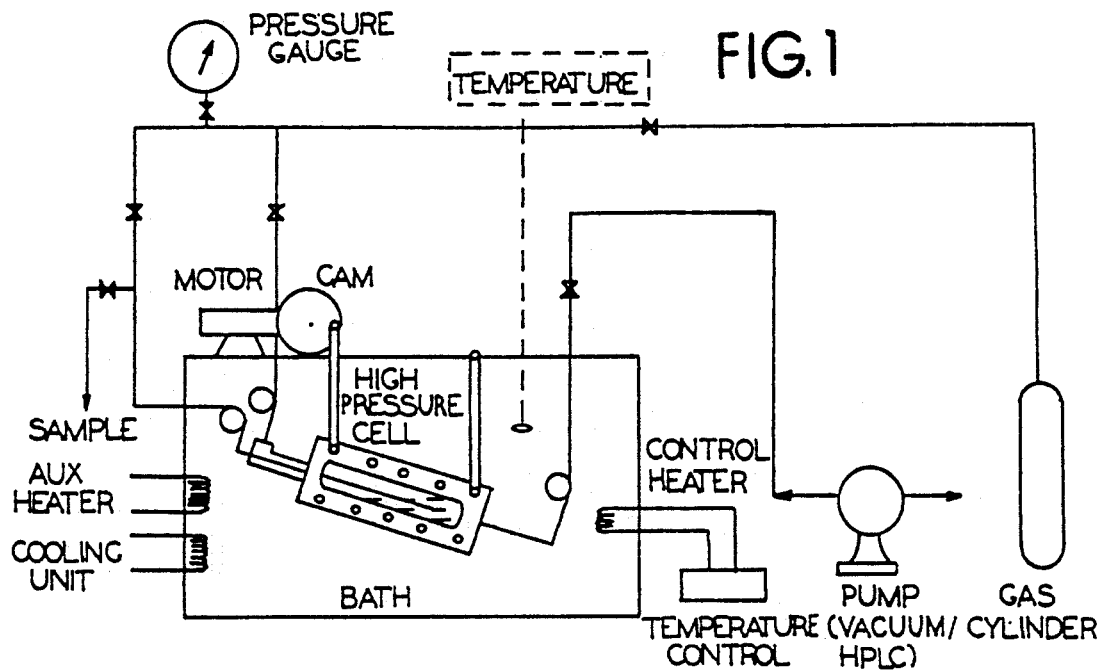
FIG. 1 is a schematic of the experimental setup.

As used herein, the term "membrane mimetic system" refers to an enclosure encapsulated by a membrane. The enclosure contains an internal reaction medium in which reaction processes take place. The membrane is a microporous structure of one or more layers of molecules which is impermeable to most macromolecules and colloidal particles. Among other structures, a membrane mimetic system refers to reversed micelles and vesicles. The term "internal reaction medium" is used interchangeably with microemulsion and solution. The encapsulated reaction medium can incorporate the same components or different components from the environment or solution outside of the enclosure.

Although many of the descriptions herein specifically refer to micelles or reversed micelles, the present invention is not so limited, and the present invention is contemplated for use with other membrane mimetic systems.

The crucial feature of the membrane mimetic system is the large surface area of the dispersed phase in comparison with the same amount of ordinary material. For instance, a 1 cm cube of material has a surface area of 6 $cm^2$; but when it is dispersed as little cubes of 10 nm size the total surface area of the resulting $10^{18}$ smaller cubes is $6 \times 10^6$ $cm^2$. This dramatic increase in the area means that surface effects are of dominating importance in the chemistry of membrane mimetic systems.

Vesicles constructed of relatively simple surfactants are membrane-like structures formed as hydrocarbon bilayers or other molecules and are considered to be spherical bags with diameters of about a few hundred angstroms (A) and a thickness of about 50 A and are osmotically active. Typically, each surfactant vesicle contains 80,000 to 100,000 surfactant molecules.

Reversed micelles, otherwise known as water-in-oil microemulsions, are usually monolayer structures having molecules with hydrophobic tails congregated and having hydrophilic heads to provide protection. Micelles are dynamically aggregated spherical structures with a diameter of about 20–30 A exceeding the critical micelles concentration and having the hydrophilic heads facing the center.

Generally, vesicles are more stable than micelles to dilution and tend not to break down. Thus, temperature induced phase transition and phase separation offer a means for permeability control and molecular recognition to thereby mimic biological membranes. More specific to this invention is that dilution or the addition of electrolytes can change the size of the model membranes. Hence, the addition of electrolyte shrinks the surfactant vesicles and placing them in solutions that are more dilute than their internal electrolyte concentrations swells the vesicles.

It is through the stability and composition of these membrane mimetic system that processes including bioseparations, polymerization, particle synthesis and drug delivery systems are conducted. By the use of hydrates associated with the membrane mimetic system in solution, the size of these membrane systems can be controlled.

It has been shown that membranes produced from polymerizable surfactants are substantially more stable upon polymerization by ultraviolet light or by the addition of initiators. As such, it is possible to prepare stable polymerized membranes in diameters that range from 300 A to 3,000 A.

The use of these species having a hydrophobic end and a hydrophilic end can form vesicle membranes by undergoing dispersion, forming multilamellar vesicles. These membranous structures have an amorphous structure of one or more separate bilayers, within each bilayer having one or more internal aqueous phase separated by a different bilayer. Upon sonication, the amorphous multilamellar vesicle transforms into a unilamellar vesicle, composed of a uniformly circular structure having the hydrophilic head facing outside the resulting membrane as well as facing the internal reaction medium within the membrane. Polymerization of the vesicle can be achieved by sonicating the species having a hydrophilic end and a hydrophobic end forming the vesicle bilayer with subsequent treatment with ultraviolet light or by the addition of initiators.

The polymerized membrane consisting of such structures as vesicles or reversed micelles, serves as efficient hosts for catalysts, semiconductors, particle synthesis, and the like due to the presence of the internal reaction medium within the membrane.

As previously discussed, the internal reaction medium of a membrane mimetic system could only be poorly controlled. The present invention seeks to solve this problem by controlling the size and concentrations of the solutes found in the internal reaction medium of the membrane mimetic system. This is accomplished by reversibly isolating a portion of the solvent present in the internal reaction medium. The result is an increase in the effective concentration of the solutes in the internal reaction medium. Thus, the internal reaction medium initially has two components: a solvent and a solute. A third component, a clathrate forming gas, is introduced to the internal reaction medium and subsequently removed.

The present invention allows a control over the size and content of micelles through the production of clathrate hydrates. When a water-in-oil microemulsion is contacted with a light gas such as methane and pressurized, some of the water in the microdroplets or micelles is converted to crystalline hydrate form which then drops out of the solution. The water content of the micelles is thereby reduced and the micelles shrink in size. By changing the system pressure, the amount of water that drops out of the solution can be controlled, thus the micelle size can be precisely controlled simply by adding or removing gas from the system. As can be understood, the process is totally reversible.

As the micelle size affects the molecular weight of a particle or product being synthesized, nanoparticle synthesis in reversed micelles is a particularly important area for the present invention. This not only allows for the production of small particles used in microelectronics, but also the efficient production of polymers and, in particular, the controlled production of colloidal size particles. The enzymatic reaction in reversed micelles can also be substantially increased by adjusting the size of the micelle. Thus, the present invention allows one to adjust the micelle size to its optimum. In addition to synthesis and enzymatic reaction, the present invention can also be used for the production of drug delivery system formulations.

As can be understood, hydrate formation can be used to remove water from the micelles and shrink the micelies, but at the same time retain other solutes such as proteins within the micelies. Thus, this provides a way of preparing small, minimal water reversed micelles with the high packing density of solutes. This is particularly useful in drug delivery systems and catalyst preparation. It is also possible to control photocatalyzed polymerization using the temperatures available for clathrate hydrates and micelies. Because particle synthesis, especially involving crystallization, is usually conducted at low temperatures, this is further facilitated by hydrate formation.

The inventive process subsequently involves reversibly isolating a portion of the solvent from the remainder of the solution. The term "isolation" means that the solvent is not physically present as a liquid in the solution or that the solvating properties of the solvent no longer substantially affect the solute, such as protein and denaturant, in the admixture. Decreasing the physical or chemical availability of the liquid solvent to the admixture increases the effective concentration of the solute. It is necessary to isolate a portion of the solvent so that the concentration of the solute is raised sufficiently to change reaction conditions in the membrane mimetic system.

The reversible isolation of a portion of the solvent is accomplished by several methods. A preferred method is to form a clathrate hydrate or a reversible precipitate with a portion of the solvent to achieve the desired isolation as discussed in more detail below.

As discussed above, one embodiment of the inventive method is to isolate a portion of the solvent by forming a clathrate hydrate. By exposing the solvent to a gas which dissolves in the solution, a clathrate hydrate is formed. The clathrate hydrate forming gas is pressurized over the solution. This causes the formation of clathrate hydrates in the solution which serves to isolate the portion of the solvent. The concentrations of the denaturant and protein increase. The proteins can now unfold, the aggregates break up, and the desired effects are accomplished.

Clathrate hydrates are crystalline inclusion compounds of gas and water. Hydrate formation is a manifestation of a hydrophobic effect where water molecules cluster around a non-polar solute (the gas species). The tendency to maintain hydrogen bonding leads to clathration of the water around the gas species. The phenomenon is thought to be stabilized by the dispersion interactions between the gas and water molecules.

Suitable clathrate hydrate forming gases include, but are not limited to, hydrocarbons having about 5 carbon atoms or less, such as methane, ethane, ethylene, acetylene, propane, 1-butene, isobutane, pentane and cyclopentane. Other suitable clathrate forming gases include xenon, nitrogen, carbon monoxide, carbon dioxide, oxygen, nitrous oxide, sulfur dioxide, sulfur hexafluoride and most of the fluorocarbon refrigerant gases. A preferred gas is methane.

The hydrate formation in a solution containing a denaturant is thermodynamically divalent (three phases: gas, liquid, and solid hydrates, and three components: water, gas, and denaturant), thus for each denaturant concentration, the system is univariant and there is a unique value of the equilibrium pressure for a given temperature. As a result, it is possible to adjust the denaturant concentration simply by increasing or decreasing the pressure at a given temperature.

For example, in a membrane mimetic system using a gas, such as methane and a denaturant, such as guanidine hydrochloride, the preferred pressure per square inch (psi) is between about 200 to about 3,000 psi with an optimum pressure being between about 400 to about 1,200 psi. This results in an effective increase in molar (M) concentration of guanidine hydrochloride in the pressurized admixture of about 4M to preferably about 6M. With other gases, different pressures are preferred. When ethylene is the gas, the pressure can be reduced to as much as about 80 psi to provide for effective unfolding and refolding of the protein.

The temperature can also be adjusted to control clathrate hydrate formation. Lowering the solution temperature usually increases the clathrate hydrate formation.

In the case of clathrate hydrates, the preferred temperature for the admixture is about $-30°$ C. to about 30° C. with a more preferred temperature between about $-10°$ C. to about 10° C. However, nothing precludes the use of both freezing and formation of clathrate hydrates through pressure. Where a combination of gas pressure and cooling are used, temperatures are preferably in the range of about $-20°$ C. to about 20° C. and optimally about $-10°$ C. to about 5° C. The associated gas (e.g. methane) pressures are preferably about 20 to about 3,000 psi and optimally about 100 to about 1,000 psi.

One of the particular advantages of clathrate hydrate formation is that it can be controlled precisely by adjusting the pressure. This means that the concentration of the denaturant and protein in the system can also be precisely controlled.

Another advantage particular to the inventive method is that it is relatively easy to repeat in a consecutive manner. If desired, the pressure of the clathrate hydrate forming gas can again be increased after the protein is refolded. The refolding process occurs again and then pressure can be released. This easy repeatability does not exist in the art, which conventionally requires the addition of more denaturant and further dilution.

The operating conditions of the inventive method are also advantageous. The hydrate formation preferably takes place at low temperatures, i.e. about $-10°$ C. to about 10° C. At low temperatures, the hydrophobic interactions are inhibited and hydrogen bonding is facilitated. During the process of depressurization and refolding, the probability of achieving the correct conformation is significantly increased by promoting intramolecular hydrogen bonding before possible intermolecular or interdomain hydrophobic interactions interfere with the desired protein folding pathway. Another feature of the inventive process is the ability to precisely control the denaturant and protein concentrations in situ through simple pressure manipulation.

A significant purpose for using the hydrate process is the competition between aggregation and correct refolding. Should aggregation persist, an alternative scheme may be used employing hydrates but encapsulating the protein in reversed micelies. Pressurization of a light hydrocarbon in the presence of bis(2-ethylhexyl) sodium sulfosuccinate (AEROSOL TO, hereafter AOT) and water, leads to solubilization and formation of reversed micelles in the dense gas phase at critical solvent density. See Nguyen, H. et al., "Clathrate Hydrate Formation in Reversed Micellular Solutions," *J. Phys. Chem.*, 93, 8123–8126 (1989); Rao, A. M. et al., "Modification of Enzyme Activity in Reversed Micelles Through Clathrate Hydrate Formation," *Biotechnol. Prog.*, 6, 465–471 (1990); Nguyen, H. et al., "Characteristics of Protein-Containing Reversed Micelles Subjected to Clathrate Hydrate Formation Conditions, *J. Phys. Chem.*, 95, 1467–1471 (1991); Phillips, J. B. et al., "Protein Recovery from Reversed Micellar Solutions Through Contact with a Pressurized Gas Phase," *Biotechnol. Prog.*, 7, 43–48 (1991). The relevant disclosures of all references cited herein are incorporated by reference.

Other methods of forming such micelles include the use of cationic surfactants, such as quaternary ammonium compounds, e.g. cetyltrimethylammonium bromide (CTAB), didecyldimethylammonium bromide (DDAB), and the use of nonionic surfactants such as hexaethyleneglycol (PEG-6).

The proteins are transferred into reversed micelles at a denaturant concentration that is sufficiently low to affect folding or to prevent transfer through salt screening of surfactant-protein interactions. Subsequent clathrate hydrate formation settles at the bulk-water interface. The nucleation of the clathrate hydrate of methane in a new environment constitutes the microaqueous phase within the reversed micelles. These water-in-oil microemulsions are capable of solubilizing a variety of compounds through encapsulation in the microaqueous phase. Micelle radii in reversed micelles can easily exceed 2.5 nm while clathrate hydrates have unit cells of sizes 1.2 nm and 1.73 nm. This implies a possibility of clathrate hydrate nucleation within the microaqueous droplets under appropriate thermodynamic conditions. The retention of protein activity in the reversed micelles allows for a number of novel reactions.

During clathrate hydrate formation, the denaturant concentration increases due to the crystallization of water. Redistribution of the solvent and solute (including denaturant) between the two phases increases the denaturant concentration in the micelles. Since the amount of intramicellar water is at least an order of magnitude smaller than the bulk aqueous phase, due to the clathrate hydrate formation, the inventive process is used to significantly increase the intramicellar concentration of denaturant, at least past the point where the proteins denature. More significantly, intermicellar collisions will increase the denaturant concentration in the micelles. Upon pressure release, the denaturant concentration decreases and the unfolded proteins are allowed to refold without aggregation. The protein refolding rate is controlled using pressure adjustment as a mechanism for manipulating the concentration.

Generally, two methods are used to encapsulate the protein aggregates into the micelles, namely the phase transfer method and the injection encapsulation method. In the preferred injection method, the protein is dissolved in the requisite amount of buffer and then stirred into a surfactant and hydrocarbon phase to yield a single-phase reversed micellar solution.

The injection method allows the protein to remain solubilized. For a two-phase system, inducing clathrate hydrate formation raises the salt concentration while the protein remain solubilized in the micellar phase. This is attributed to the fact that, at the low temperatures of hydrate formation, the reduced ionic mobilities inhibit salt penetration between the micelle interface and protein to screen out protein-surfactant interactions.

Alternatively, a single-phase system can be used if protein solubility is not viable in the two-phase system. The single phase process encapsulates the proteins in relatively large micelles with an initial water to surfactant molar ratio $w_o$ of 20, which contains a low denaturant concentration. The ratio of water to surfactant, $w_o$, is the characteristic quantity that influences the size and aggregation number of the micelles. See, Zulauf, M. et al., "Inverted Micelles and Microemulsions in the Ternary System $H_2O$ Aerosol-TO/Isooctane As Studied by Photon Correlation Spectroscopy," *J. Phys. Chem.* 83, 480–486, (1979). The formation of clathrate hydrates and removal of intramicellar water decreases the micelles' size, but also in the process increases denaturant concentration and thus denatures the proteins and breaks aggregates. Upon pressure decrease, the hydrates dissociate and the water release is spontaneously reincorporated into the micelles, increasing the micelles' size, lowering denaturant concentrations and allowing the proteins to refold.

Clathrate hydrates can form in single phase reversed micellar systems and, during this process, water is removed and the micelles' size is changed. Protein solubility is retained in the micelles even if the intramicellar concentration of the solute increases through clathrate hydrate formation. It is believed that this results from the inability of the ions to screen out established protein-surfactant interactions in small micelles.

If large micelles are introduced into the clathrate hydrate cell and the cell is progressively pressurized at constant temperature, then clathrate hydrates progressively form and reduce the micellar size. The process is completely reversible. By decreasing the pressure, clathrate hydrates dissociate and the released solvent is spontaneously reincorporated into the micelles, increasing the micelles' size, lowering the denaturant concentration and allowing the proteins to unfold.

An apparatus for use with the present invention is shown schematically in FIG. 1. A glass-windowed high-pressure cell is suspended in a bath and agitated by a motor and cam arrangement to maintain uniform dispersement of the cell contents. Stainless steel beads (not shown) in the cell further aid the mixing of the cell contents. A water and methanol mixture is suitable for use as the bath liquid. The temperature of the bath is controlled by auxiliary heating and cooling elements in combination with a conventional temperature control unit. Sampling tubes are inserted into the top and bottom of the cell to sample the phases and control the atmospheres in the cell. The atmosphere in the cell is controlled by a pump. A clathrate hydrate forming gas is introduced from a gas cylinder. The pressure of the cells' atmosphere is monitored by a gauge.

Protein conformation changes can be monitored in situ using fiber optic probes in high pressure cells or by setting up the reaction in the sampling cell of the appropriate spectrometers. The presence of clathrate hydrates prevents the use of spectroscopy using beams, particularly those measuring light intensity, because the hydrates absorb the light. Fourier transform methods have been shown to be available in this analysis. Further, in situ analysis can be conducted using magnetic resonance methods, particularly magnetic resonance and electron spin resonance.

Analysis is performed using ultraviolet-visible and fluorescence spectrophotometry, and in the case of protein aggregates, the analysis also uses dynamic light scattering and size exclusion High Performance Liquid Chromatography (HPLC). Absorbance and fluorescence spectroscopies are simple and widely used spectroscopies to characterize protein folding since the absorption and fluorescence spectra of a chromophobe are very sensitive to the solvent environment.

The absorbance and fluorescence data is interpreted by using simple denaturant curve analysis applying the equilibrium constant for folding, $K_D = \exp(-\Delta G_D/RT) = f_D/f_N = (Y - Y_N)/(Y - Y_D)$, where $\Delta G_D$ is the Gibbs free energy of folding, D and N refer to the denatured and native protein states, and y is the measured characteristic (e.g. the absorbance or fluorescence intensity).

Light scattering analysis was also performed to identify protein aggregates by obtaining the mean particle sizes and particle size distributions through a polydispersity index, using standard cumulant techniques. In the light scattering tests, a Coherent Innova 90-5 argon ion laser operating at 488 nm was used in conjunction with a Thorn EMI head-on phototube for single photon counting and a Brookhaven BI 2030 auto correlator. For HPLC analysis, a Perkin-Elmer instrument fitted with a binary gradient pump and a diode array detector was employed. The HPLC analysis was made through a DuPont Zorbax GF-250 column, with the mobile phase consisting of a denaturant-containing-buffer, and detection at 220 nm.

This invention relates to the effects of controlling membranous size by using pressurized gas in contact with a membrane mimetic system. See John, V. T. et al., "Pressurized Gases in Contact with Liquid Reversed Micellar Solutions: Effects on Micellar Size and Stability, and Biotechnological Applications," *Proceedings of the Second International Symposium on Supercritical Fluids*, 70-73 (1991), the pertinent disclosures of which are incorporated herein by references.

This invention also relates to the application of membrane mimetic systems for synthesizing particles, particularly semiconductor particles. See Kortan, A. R. et al., "Nucleation and Growth of CdSe on ZnS Quantum Crystallite Seeds, and Vice Versa, in Inverse Micelle Media," *J. Am. Chem. Soc.*, 112, 1327-1332 (1990). Further, this invention teaches an alternative method for polymer synthesis using membrane mimetic systems. See F. Candau et al., "Inverse Microlatexes: Mechanism of Formation and Characterization" and Wiley's *Encyclopedia of Polymer Science and Engineering*, 2nd ed.

Of particular interest is the use of the present invention for enzymatic polymer synthesis in an organized medium within a membrane mimetic system such as a reversed micellar solution. The targeted products are water-soluble such that the reaction medium within the reversed micelles control the molecular weight distribution of the polymer, hence, allowing for uniform distribution.

The presence of hydrate in this process has the desirable effect of monitoring the micellar size. This mechanism enables the control of the polymer synthesis by regulating the molecular weight distribution. Further, after a predetermined molecular weight is encapsulated within the micellar structure, subsequent hydrate formation has the effect of extracting the polymers formed in the process.

Polymerization in the reversed micelles has a particular advantage over emulsion polymerization, in which polymers are formed directly in water. Unlike the instant invention, the emulsion polymerization technique causes reactive complications such as instability of the lattices resulting in rapid sedimentation of the polymer and a broad size distribution of the final particles. The application of reversed micelles overcomes the problem caused by polymerization.

In the inventive process, the monomer is emulsified in a reactive medium such as water with the aid of emulsifying agents. These agents can take the form of anionic and nonionic surfactants.

For example, one such anionic surfactant used in stabilizing the polymers is sodium bis(2-ethylhexyl) sulfosuccinate (AOT). The monomer acts as a cosurfactant and is partially located at the water-oil interface, which relates to a strong increase of the attractive interparticular forces with the monomer content in the system. The process is characterized by high reaction rates and by high molecular weights.

The mechanism involved is continuous particle nucleation. The resulting polymer is comprised of the fusion of about 60 to about 150 micelies. Each final latex particle contains an average of about one single polymer in a collapsed state as compared to the thousands of chains in the inverse lattices.

Nonionic surfactants may be used in inverse emulsion polymerization. The emulsifiers for polymerization comes in the form of blends, where the most desirable ratio for hydrophile-lipophile is experimentally predictable. For example, a blend of sesquioleate sorbitan and polyoxyethylene sorbitol hexaoleate is desirable for the microemulsification of an aqueous solution of acrylamide or acrylamide-sodium acrylate in an isoparaffinic oil. Further, polymerization of acrylamide has been performed in water-toluene systems stabilized by amphiphilic block copolymers in the presence of 2-propanol.

The present invention is of particular use to synthesize polymers of high molecular weight and water-soluble polymers. These polymers include polyacrylamide and its derivatives. These polymers are of particular utility in various applications such as surface coatings, adhesives, and photographic emulsions.

Photographic emulsions are not true emulsions, but suspensions of minute silver halide crystals or other light-sensitive, image-creating materials, dispersed in a protective colloid medium as gelatin, collodion, albumen, casein or agar. Gelatin is preferred as a photographic colloid because the sensitizing bodies present in the gelatin make possible emulsions with greater sensitivity or speed. Gelatin is an excellent emulsifying agent. It is readily transformed from a gel form to a liquid form, or the reverse, by changes in temperature. The latter property makes coating of supports, in emulsion processing and working, feasible. The strong protective action of gelatin lowers the rate of reduction of unexposed silver halide crystals in developers so that image formation is readily obtained.

The basic procedure in the method of preparing a commercial emulsion includes swelling a portion of the gelatin in the formula by soaking it in water and later dissolving it with heat. Mixtures of soluble potassium iodides or chlorides are placed in water solution and added to the gelatin solution. Precipitation of silver halide is accomplished by slowly adding a solution of silver nitrate, while stirring, to the mixture. The relative concentration of the solutions, the rate of addition, and temperature during mixing, are factors which control the size, formation and dispersion of the crystals in gelatin. The emulsion is then heated or "ripened" at about 40° C. to about 50° C. to recrystallize the silver halide and readjust the size-frequency distribution. Following ripening, more gelatin is added and the emulsion is chilled so it will set quickly.

The emulsion is then placed in a press and forced through a screen to break it into shreds which are washed in cold running water to remove the potassium nitrate formed, the excess soluble halide, and certain soluble by-products of the reaction. Chloride emulsions are often prepared without washing or with only a limited washing. After washing, the emulsion is drained, remelted, and certain agents, such as fog preventatives, are added. The emulsion is then heated, or "after-ripened," to form sensitizing nuclei on the silver halide crystals. This operation increases the sensitivity in contrast of the emulsion and is necessary for the preparation of high-speed negative emulsions. Certain preservatives, or stabilizers, are added so the emulsion can be stored in refrigerated rooms until needed.

Before coating, sensitizing dyes, hardening agents, wetting agents, etc., are added to the emulsion. After a thorough mixing, filtering, and heating to coating temperature, the emulsion is placed in a coating machine. Supports, such as film, paper, or glass, and substrate coatings are fed through the coating machines at proper rates so they become coated with emulsions in uniform layers of desired thickness. The coated supports are passed over chilled boxes to set the emulsion and then through a series of drying compartments where the rate of drying is carefully controlled so as not to change the emulsion's sensitivity on the surface.

Following drying, the coatings are inspected under proper safe lights and the film or paper is cut to the desired size and packaged. The palladium and platinum processes employ iron salts as the primary light-sensitive material and from the standpoint of photochemistry should be considered as palladium-iron and platinum-iron processes.

Particles synthesized in the reversed micelles can be removed through hydrate formation in the micelies. The hydrates take out water from the micelles and decrease the micelies' size. The consequent shrinkage of the micelles leads to ejection of nanocluster particles in the micelles and consequent precipitation of the particles.

In addition to synthesizing semiconductor particles such as the sulfides and selenides of zinc and cadmium, other types of particles can be synthesized in reversed micelies. For example, synthesized catalyst particles of platinum (Pt) and palladium (Pd) type particles can be later precipitated onto a solid support, and synthesized colloidal particles can be used for catalytic coatings.

Enzymatic polymer synthesis in the reversed micelles with polymers that are water-soluble allows the microvolume of the micelles to control their molecular weight distribution and leads to a uniform distribution. Sample polymers are polyacrylamide, polymethylmethacrylate. Again, controlling the micelies' size by hydrate formation can have a desirable affect on the polymer synthesis in terms of molecular weight distribution. Also, hydrate formation can squeeze the polymers out of the micelles after they have reached a certain molecular weight. These polymers can be used in surface coatings, adhesives, photographic emulsions, etc. A polymer formed in reversed micelles as disclosed herein generally has better morphological properties than when the same polymer is formed by inverse polymerization in water.

By practicing the present invention, phenolic and aromatic amine containing polymers have been synthesized with the functional groups on the polymer aligned leading to an oriented polymer having unique properties. Orientation on the polymer is imposed by orienting the individual monomeric units prior to synthesis. The monomers have surfactant properties (i.e., they are amphiphilic). This suggests that in reversed micellar systems they would be oriented at the oil-water interface of the microdroplets with the functional groups (hydroxyl and/or amine) inside the water pools. The micelle contains the catalytic enzyme, such as peroxidase, tyrosinase, laccase or the like, which is then used to close the monomer on the interface.

The present membrane mimetic system can be used to not only synthesize polymers efficiently by enzyme-based polymerization reaction in reversed micellar solution, but to also control the size and morphology of the polymer particles formed. By appropriately adjusting the composition of the reaction medium and by controlling the amount of any added reaction mediating compound, such as hydrogen peroxide, supplied externally or generated in situ, the size of the finely dispersed polymer particles formed can be adjusted. In particular, spherical particles of micron and submicron size can be formed when the polymerization reaction is effected in reversed micelles containing a liquid hydrocarbon solvent and a surfactant. The polymers thus enzymatically synthesized at a surfactant concentration of from at least 0.01M have definite morphologies as opposed to those of comparable polymers synthesized in monophasic organic solvents.

In one preferred polymer synthesis embodiment, the enzyme concentration can range upwards from a minimum of about 0.1 mg/ml; and the substrate (monomer) concentration can range from a monomer to surfactant ratio of about 0.1 to about 10 upwards to a monomer to surfactant ratio of about 10 to about 1. A preferred reaction mediating compound is a source of hydrogen peroxide but is not limited thereto. Preferably liquid hydrogen peroxide is added to provide a molar concentration in excess of the monomer concentration. Alternatively, the reaction mediating compound can be generated in situ. For example, glucose oxidase can be encapsulated along with peroxidase, in the reversed micelles and glucose added to generate hydrogen peroxide in situ. To date it has also been found that the catalytic enzyme, tyrosinase, does not require added hydrogen peroxide to catalyze the polymerization.

Finely divided spherical polymer particles are useful in commercial applications as antiflocculants, dispersion agents and viscosity modifiers.

The present invention has been practiced to synthesize polymers having high molecular weights (>about 400,000), high thermal and mechanical strengths, and most importantly, possessing non-linear optical properties. Applications involve their use in optonics (optical switching and wave-guides) and laser protection material. These polymers can also be developed into electrically conductive materials with applications to electronics. Such conductive polymers have significant applications in electro-optics. If these polymers are chelated with metals, they can be used for a variety of other applications.

Finely divided spherical polymeric particles of micron and submicron size can be used in chromatography. Because small spherical particles have an effectively large surface area, the polymers are particularly suited as packing materials in chromatography columns. For affinity type separation columns, the type of compounds to be separated are controlled by the specific ligands on the polymer. For metal affinity type separations, metals can be chelated onto the polymers.

If the metal chelated onto the polymer is catalytic, the entire polymer-metal composite can be used as a heterogeneous catalyst activity. For example, if copper is the chelating metal, there is a potential application for using such polymer supported metal catalysts in the breakdown of organophosphorus compounds (e.g. insecticides, pesticides, etc.).

The polymers may be used as barrier films for chemical remediation and decontamination. The films and finishes made of these polymers can be used to bind heavy, radionuclides and organic chemical contaminants. The functionality of the films and finishes can be improved by controlling the pore structure of the film and improving the effective surface area for adsorption and binding. These characteristics are particularly improved by using finely dispersed particles as the starting materials for film and finish formation.

Various functionalized materials can be encapsulated within the spherical polymer particles. Some examples of these inclusion materials include ceramic nanoparticles, semiconductor nanoparticles or biocompounds such as proteins or drugs. The material to be encapsulated is first placed in the water core of the reversed micelles, then the polymerization is conducted around the periphery of the micelles. In the process, the material in the water core becomes encapsulated.

Various applications for functionalized materials encapsulated within the polymer particles include timed released/slow release drug delivery systems, encapsulated semiconductor nanoparticles stabilized against aggregation and growth for electronic and electro-optic applications, and high-performance polymer-ceramic composites. The electro-optic properties of these conductive polymers can be further enhanced by the encapsulation and/or impregnation of electro-optic semiconductor particles. The resultant polymer-semiconductor composites can be fabricated in desired geometries for various electro-optics applications.

Environmental applications are also available wherein polymers can be used as adsorbents of organic materials. Because of the amphiphilic groups on the polymers, they can be used to adsorb a variety of organic compounds. The small size of the particles indicate that they can be immobilized within hollow fiber membranes. Applications include cleanup of waste water streams and biological degradation of organic chemicals.

Another environmental application of this invention is the removal of phenolic and aromatic amine contaminants from aqueous streams by polymerizing them to insoluble polymers and thus precipitating them from aqueous solution. Surfactants can be added to concentrate the contaminants from the aqueous streams and the contaminants are then encapsulated into micelles. The enzymes can then polymerize the micelles and take the polymers containing the contaminants out of the solution. The contaminants can then be isolated since the surfactants biodegrade and are much shorter lived than the contaminants.

Biomedical applications of these polymers using imaging technology are available. Because the polymeric particles can be hollow inside, contrast agents for magnetic resonance imaging can be incorporated therein, particularly for targeting specific organs.

Under certain conditions, practicing the present invention formed a very clear novel gel which was highly moisture sensitive and, on being exposed to air, liquefied in about two hours. In one aspect, this means that the gel can be used as a humidity sensor in environments that require a low humidity. For example, individual reactants can be included in the gel separately at different positions so that when the humidity exceeds a certain level, the gel liquefies and allows the reactants to contact each other leading to a color change.

In another aspect, the gel can be used for particle and polymer synthesis within the gel. For example, the gel is formed by adding AOT (the surfactant), isooctane (the solvent), and a phenolic compound (e.g. p-ethylphenol). There is no water initially present. One of the components of the gel (e.g. p-ethylphenol) is a substrate for polymerization. Gelatin can also be added to gel the reversed micellar solution and enzymatic polymer synthesis can be carried out in the gel. Also in the gel, the molecules can be arranged in specific orientations to synthesize further novel polymers upon doing the polymerization and to prolong polymer growth time. Particle synthesis in these gels is contemplated by the present invention to produce monodispersed nanoparticles. These gels and other products synthesized hereby can be used as topical drug delivery systems according to the procedures disclosed in the references cited herein.

EXAMPLE I

This example illustrates two membrane mimetic systems prepared from enzyme-encapsulated reversed micellar solutions of lipase and α-chymotrypsin and gas hydrates.

The enzymes, lipase from *Candida cylindracea*, and α-chymotrypsin, the substrates oleic acid and N-glutaryl-L-phenylalanine-p-nitroanilide (GPNA) were obtained from Sigma Chemical Co.; and octanol was obtained from Aldrich Chemical Co. Reversed micelle constituents included the anionic surfactant bis(2-ethylhexyl) sulfosuccinate sodium salt (AOT) and isooctane (99% purity), both obtained from Aldrich. Methane (>99.9% purity, Matheson) was used as the hydrate-forming gas. Double-distilled water was used in buffer preparations.

Enzyme-encapsulated reversed micellar solutions were prepared by the injection method generally as follows. Each individual enzyme was first separately dissolved in aqueous buffer at its appropriate respective pH; namely, pH 7.5 for lipase in 0.01 M phosphate buffer and pH 10.5 for α-chymotrypsin in 0.1M glycine/NaOH buffer. Each enzyme-containing aqueous phase was then individually and separately contacted with isooctane containing AOT dissolved therein at the given concentration discussed below. Each mixture was stirred with a magnetic stirrer until an optically transparent reversed micellar solution was obtained.

The apparatus used to conduct hydrate formation in reversed micelles is shown schematically in FIG. 1. The apparatus uses a glass-windowed, high-pressure cell. suspended in a temperature-controlled methanol/water bath and is rocked to maintain agitation of the cell contents. Sampling tubes inserted into the cell enable removal of the liquid phase at high pressure.

Activity measurements for lipase catalysis in reversed micelles were carried out at about 313 degrees Kelvin (K.). The reaction was conducted in a shake flask set in a water bath, and samples were analyzed as a function of time through gas chromatography (flame ionization detection, 15-m capillary column, methylsilicone stationary phase, 1.5-μm film thickness). Since extremely good resolutions and peak reproducibilities were obtained for alcohol (octanol) and solvent (isooctane), the ratio of the octanol to isooctane peak areas was simply used as the measure of alcohol conversion and reaction progress.

A 1:1 molar ratio of oleic acid and alcohol was used in all examples; thus the alcohol conversion was directly related to the acid conversion and the ester yield. For α-chymotrypsin, the procedure followed was described specifically by Barbaric et al., in *J. Am. Chem. Soc.*, 103:4239-4244 (1981) and generally by Luisi, P. L. in *Reverse Micelies*, published by Plenum N.Y. (1984). This procedure involved introducing into the sample cell of a UV spectrophotometer 0.3 ml of enzyme-containing reversed micelles of a given $w_o$ and 1.2 ml of substrate (GPNA) containing micelles of the same $w_o$, to give 1.5 ml of solution with final substrate and enzyme concentrations of 0.2 mM and 1.3 μM, respectively.

The same procedure was followed for the reference cell with the exception that the 0.3 ml of reversed micellar solution did not contain any enzyme. The difference between the two cells was only the enzyme content. The reaction was followed by monitoring the absorbance at 366 nm due to the nitroaniline released during the process. See also Luisi, "Enzymes Hosted in Reverse Micelles in Hydrocarbon Solution" *Angew. Chem , Int Ed Engl*, 24, 439-450 (1985), incorporated herein by reference. The slope of the absorbance vs time plot, linear over the first 15 minutes, was used to determine initial results.

Figure 2:
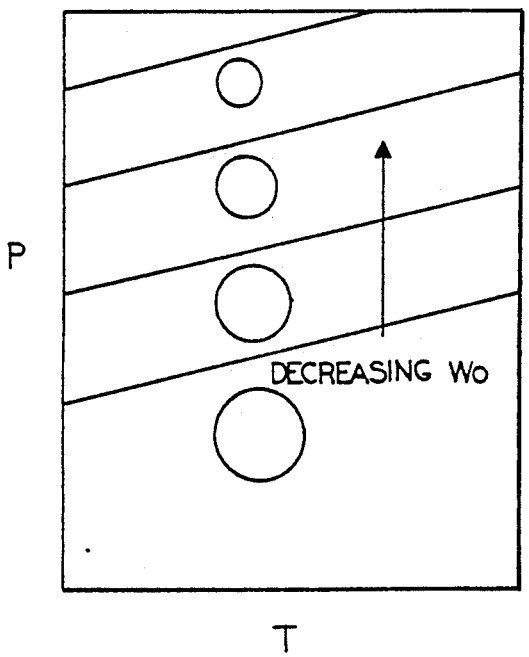
FIG. 2 summarizes the characteristics of hydrate formation in reversed micelles and each line represents the univariant P-T correlation of a specified $w_o$.

FIG. 2 summarizes the essence of hydrate thermodynamics in reversed micelies. See Nguyen et al., *J. Phys. Chem.*, 93, 8123-8126, (1989) for data and background information on hydrate formation thermodynamics. Hydrate formation was dependent on the water to surfactant ratio, $w_o$, and was independent of the amount of surfactant. At each $w_o$, the system was univariant, as represented by the pressure v. temperature (P-T) line for a given micellar size (or $w_o$) in FIG. 2; i.e., the pressure at which hydrates form was determined once the temperature was specified. This equilibrium pressure, or dissociation pressure as it is termed, increases as $w_o$ decreases, i.e., as the micelles decrease in size. The smaller the micelies, the more bound the water molecules and the greater the chemical potential induced driving force, manifested as the pressure required to reorient the water molecules to the hydrate crystalline form.

Figure 3:
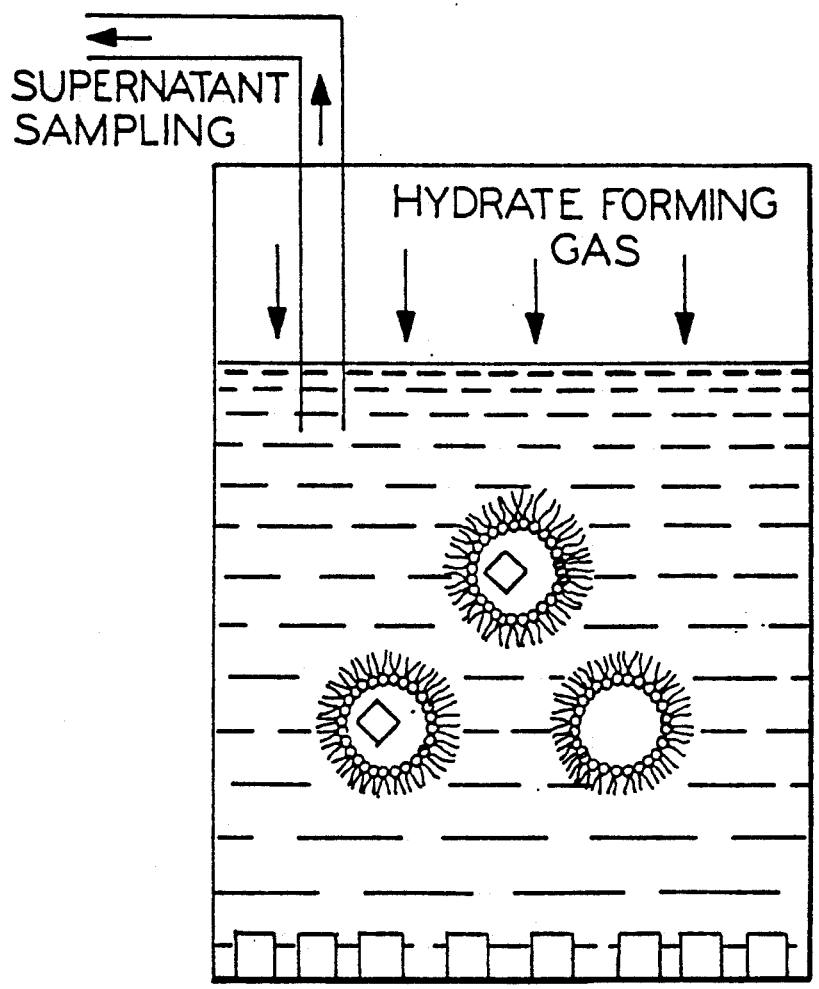
FIG. 3 is a schematic of the contents of the hydrate cell.

The situation in the hydrate cell is represented schematically in FIG. 3. As hydrates formed and nucleated, they settled to the bottom of the cell (hydrates being more dense than the bulk organic) allowing sampling of the protein-containing micellar supernatant.

Examining FIG. 2 from another aspect, if large reversed micelles are introduced into the hydrate cell and the cell is progressively pressurized at a constant temperature, then hydrates progressively form and reduce the micellar size. The procedure was completely reversible. By decreasing the pressure, hydrates dissociated and the water released was spontaneously reincorporated into the micelles to increase their size. Knowledge of the pressure v. temperature data and size v. $w_o$ correlations thus allows alteration of micellar size to a desired value by manipulating the pressure at a given temperature.

See, for example, Nguyen et al., "Characteristics of Protein-Containing Reversed Micelles Subjected to Clathrate Hydrate Formation Conditions" *J. Phys. Chem.* 95, 1467-1471 (1991); Pileni et al, "Solubilization by Reversed Micelies: Solute Localization and Structure Perturbation" *Chem. Phys. Lett.*, 118, 414-420 (1985); van der Waals and Platteeuw, "Clathrate Solutions", *Chem. Phys.*, 2, 1-57 (1959).

Protein extraction from a fermentation broth entered into reversed micelles through phase transfer involves contacting the broth with a reversed micellar solution constituting a separate phase. See generally, Rahaman et al., "Recovery of an Extracellular Alkaline Protease from Whole Fermentation Broth Using Reversed Micelles," *Biotechnol. Prog,* 4, 218-224 (1988); Göklen et al., "Protein Extraction Using Reverse Micelies," *Biotechnol. Prog.*, 1, 69-74 (1985). A maximum amount of water is solubilized into the micelles which will then exist at the maximum $w_o$ dictated by the ionic strength and pH of the aqueous solution. $w_o$ values of reversed micelles in contact with a bulk aqueous phase are typically above about 20. For example, our test results through Karl-Fischer titration (Mettler DL-18) demonstrated that the $w_o$ of reversed micelles in contact with an aqueous phase containing 0.1 M KCl and pH 7 was about 24.

In order to form hydrates at a reasonable pressure, the system was cooled to temperatures approaching about 273 degrees K. For example, hydrate dissociation pressure when methane was used as the hydrate forming gas at about 273.15 degrees K., was 2.76 MPa for reversed micelles with a $w_o$ of about 15; 3.10 MPa for micelles with a $w_o$ of about 10; and 4.83 MPa for micelles with a $w_o$ of about 5. There is thus the need to maintain enzyme activity at low temperatures. Additionally, sampling was done carefully to avoid deactivating the enzyme through shearing during the process.

The process of pressurizing a sampling to 0.1-0.3 MPa below the temperature-controlled hydrate cell and recovering the supernatant across this small pressure gradient results in a sample with little enzyme deactivation. Once the sample was recovered, the pressure in the sampling cell was slowly reduced to atmospheric pressure substantially without destroying enzyme activity. Considerably lower pressures can be used with other gases; for example, xenon forms hydrates in reversed micelles of a $w_o$ of about 15 at about 0.19 MPa and about 273.15K.; the corresponding dissociation pressure for ethylene hydrates is 0.62 MPa. The following hydrates were prepared with methane as the hydrate forming gas species, but is not limited thereto. Protein solubility was completely retained during methane hydrate formation at the chosen temperature (about 273.15K.) and pressures (up to about 6 MPa).

Figure 4:
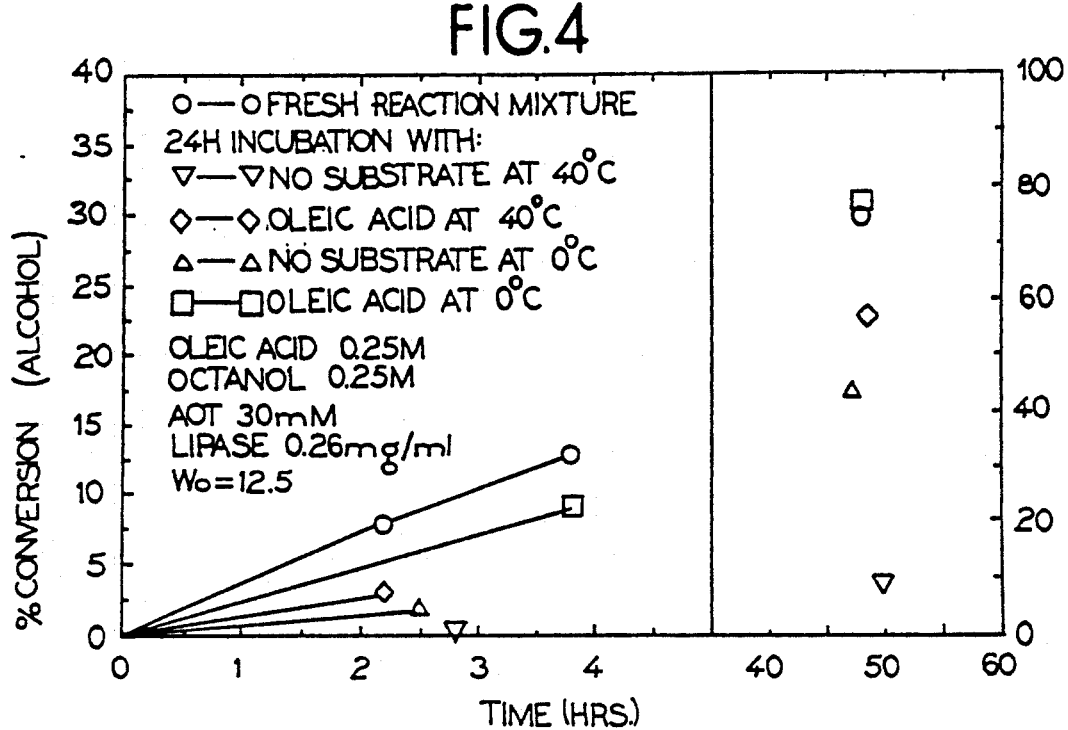
FIG. 4 illustrates lipase activity maintenance through acyl-enzyme coupling.

Lipase-catalyzed ester synthesis is a bimolecular reaction involving the substrates oleic acid and octanol. Since both substrates are amphiphilic, reaction proceeds at the interface of the micelle. It was found that the enzyme rapidly loses its activity in reversed micelles unless it is contacted with the acyl substrate, oleic acid as illustrated in FIG. 4. The fresh reaction mixture (filled circles in FIG. 4) denotes the case where the reaction was started by adding both substrates immediately following encapsulation of the enzyme. Incubating the encapsulated enzyme at about 313K. for 24 hours prior to staring the reaction by adding the substrates results in a significantly less active enzyme; the loss of activity was somewhat mitigated by incubation at about 273 K. On the other hand, incubation with the acyl substrate for 24 hours prior to reaction initiation by adding the alcohol results in activity maintenance. Furthermore, the activity was well maintained when incubation with the acyl substrate is carried out at about 273K. rather than at about 313 K. Indeed, a 2-day incubation run at about 273K. also showed good maintenance of activity.

The use of the acyl substrate in stabilizing the enzyme appears reasonable when one considers that the mechanism for lipase catalysis involves initial binding to the acyl substrate as set forth generally by Deleuze et al., in Biochim. Biophys. Acta, 911, 117-120 (1987):

where AcX and AcY re the acyl donors (the acid and ester, respectively), AcE is the acyl-enzyme complex, and X and Y are the nucleophilic acyl acceptors (water and alcohol, respectively). Thus, the acyl-enzyme binding may optimally position the enzyme at the interface allowing activity maintenance.

The acyl-enzyme coupling was important in experiments involving hydrates, since the process of hydrate formation and sampling at progressively higher pressures took place over the course of a day or two. Accordingly, the initial sample introduced to the hydrate cell was a lipase-containing reversed micellar solution of $w_o$ about 24 and oleic acid content 0.05M. The presence of the amphiphilic substrate then changed the nature of the micelle, and the pressure v. temperature v. $w_o$ diagram generated for single-surfactant micelles was no longer applicable for the added cosurfactant case. That is, it was not possible to determine simply from the pressure (at a given temperature) what the $w_o$ of the micellar supernatant was, unless a new pressure v. temperature v. $w_o$ diagram was generated for the dual surfactant case. Once the samples were removed from the hydrate cell, they were contacted with 0.05M octanol to initiate reaction, which was carried out in a shake flask maintained at about 313 K.

Figure 5:
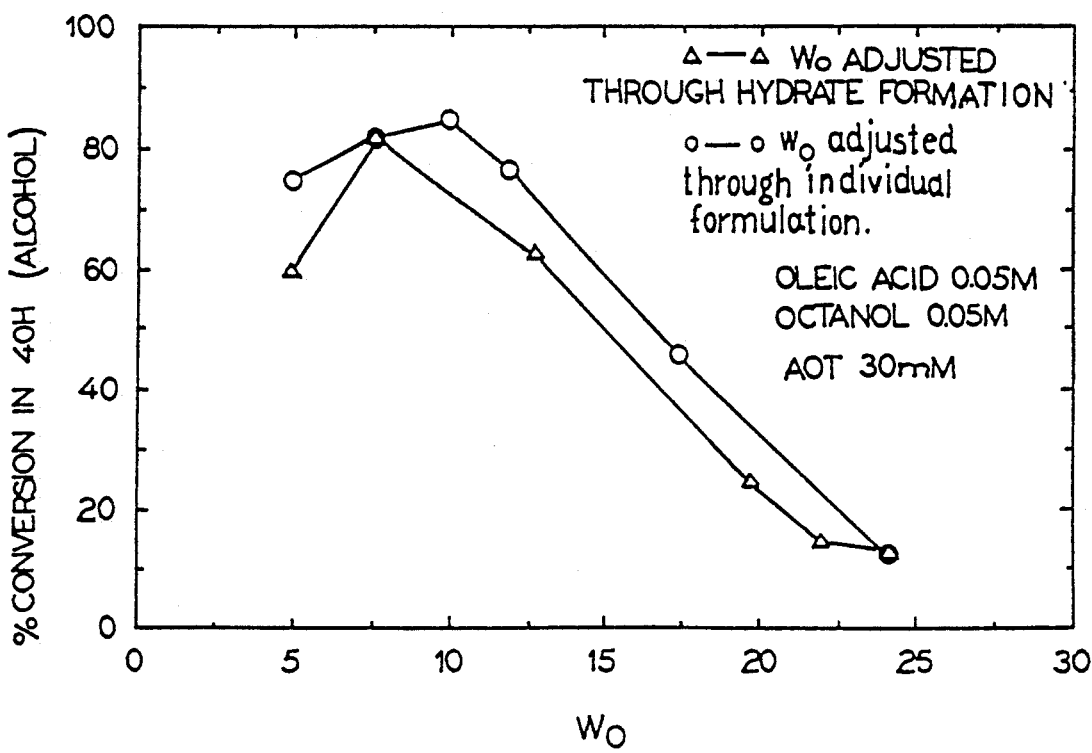
FIG. 5 illustrates lipase activity modifications through hydrate formation.

FIG. 5 illustrates the lipase activity obtained from reversed micelle samples recovered from the hydrate cell at different $w_o$ values over a pressure range of 2.7-7 MPa at about 273.7K., starting with an initial solution of a $w_o$ about 24. The activities were compared to those obtained from lipase-containing micellar solutions, individually prepared at different $w_o$ values. The maximum activity for the hydrate-modified case was very slightly lower than that for the individual preparation case, and the optimal $w_o$ appeared to be shifted to a lower value. The fact that lipases in reversed micelles exhibited a significant enhancement of activity when the $w_o$ was modified by hydrate formation was indicative of the fact that hydrate formation in the micelles did not lead to enzyme deactivation. The apparent shift in optimal $w_o$ appeared to be the result of changes in the microaqueous environment brought about when apart of the micellar water was removed through hydrate formation.

With α-chymotrypsin, the reaction was quite different. Although the hydrolysis of GPNA was also bimolecular, one of the substrates (water) was a constituent of the micelies. At the GNPA concentrations used (0.2 mM), less than 0.1% of the micellar water was required for full conversion. The large excess of micellar water implied that there was no effect of the reaction on the $w_o$ of the solution. The hydrate formation test was simply carried out by introducing an enzyme-containing reversed micellar solution at a $w_o$ of about 17, forming hydrates at progressively higher pressures and sampling the supernatant at different pressures. The pressure v. temperature v. $w_o$ data developed for empty micelles held well for this system, and the $w_o$ of the supernatant was determined simply by noting the equilibrated pressure, which was also verified by Karl-Fischer titration. As soon as a supernatant sample was taken from the hydrate cell and its $w_o$ measured, the enzyme activity was assayed.

Figure 6:
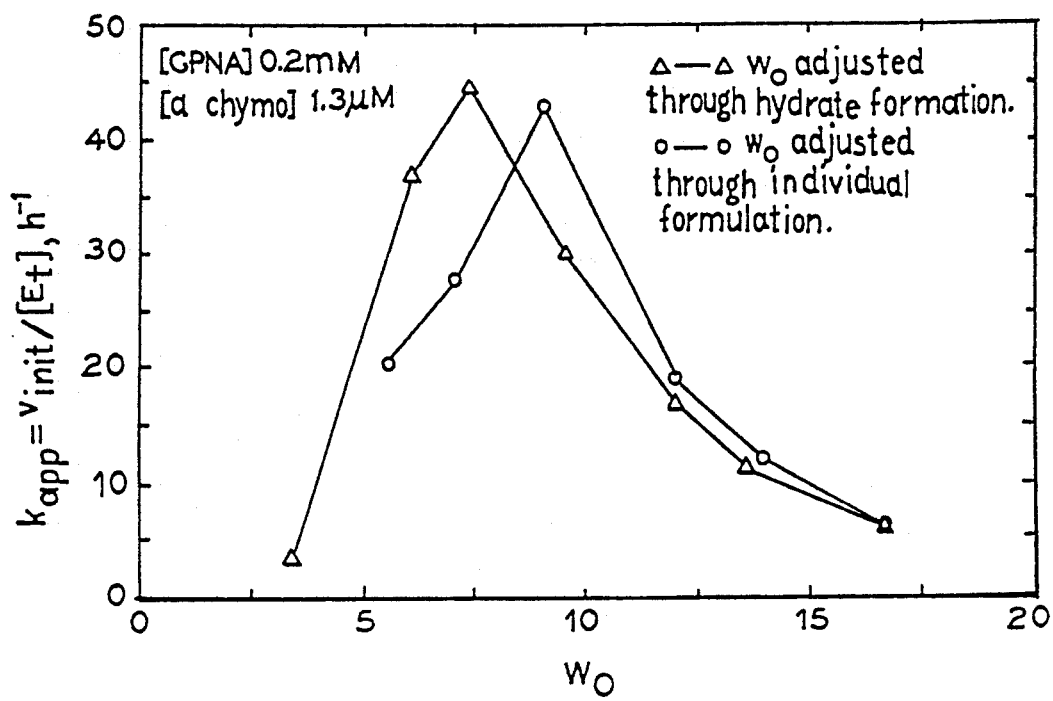
FIG. 6 illustrates α-chymotrypsin activity modifications through hydrate formation where $k_{app}$ is the apparent rate constant, $V_{init}$, the initial rate and $E_t$, the total enzyme concentration.

FIG. 6 is similar to FIG. 5 and illustrates the α-chymotrypsin activities in micelles of different $w_o$ values, where $w_o$ was adjusted either through individual sample preparation or through hydrate formation. Again, the hydrate formation technique of adjusting $w_o$ led to enzyme activity modifications; the comparable activity in both cases implied that hydrate formation within the micelles did not adversely affect enzyme activity. The small shift to a lower optimal $w_o$ was observed, which was attributed to changes in the microaqueous phase. The optimal $w_o$ for α-chymotrypsin can be a function of the pH of the buffer from which the micellar solution was prepared. The acidity of the modified microaqueous phase can be examined by using the method of $31^P$ NMR analysis. See generally Smith et al., "Micellar Solubilization of Biopolymers in Hydrocarbon Solvents. III. Empirical Definition of an Acidity Scale in Reverse Micelies," Helv. Chim. Acta, 63:2302-2311 (1980).

Figure 7:
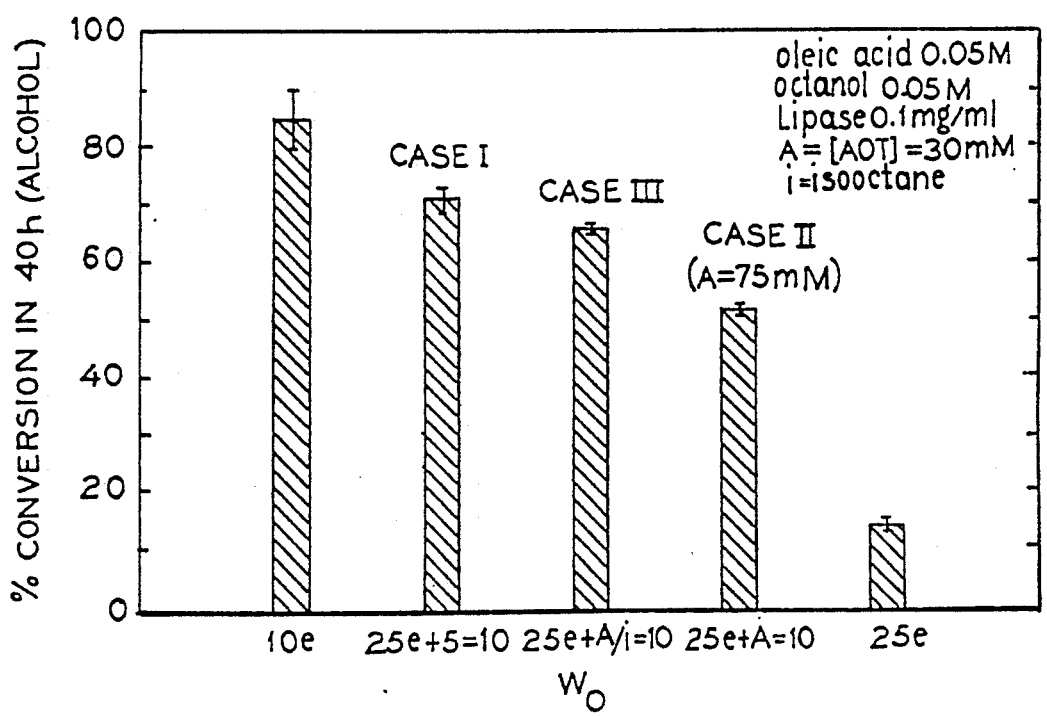
FIG. 7 illustrates alternate methods of changing $w_o$ and effects on lipase activity, in which the notation 25e, for example, indicates enzyme containing micelles of $w_O=25$.

Hydrate formation in enzyme-containing reversed micelles leads to a change in micelle size and a concomitant modification of enzyme activity. Three cases (Case I, II and III) involving other methods of changing $w_o$ and the effect on enzyme activity are illustrated in FIG. 7 for lipase and in FIG. 8 for α-chymotrypsin.

In Case I empty reversed micelles of much smaller $w_o$ (small micelies) were added to enzyme-containing micelles of higher $w_o$ to yield a micellar solution of the optimal $w_o$. For example, mixing micellar solutions of a $w_o$ of about 5 and a $w_o$ of about 25 in the volume ratio 3/1 leads to a solution with a $w_o$ of about 10 (FIG. 7). When the enzyme was originally contained in micelles of a $w_o$ of about 25, the procedure resulted in a 3-fold reduction of the enzyme concentration and hence a reduction in total reaction rate. For comparisons of the different cases, the enzyme concentration was adjusted in making up the solutions of a high $w_o$, so that the final enzyme concentrations were the same in all cases. The notation 25e+5 denotes the mixing of micelles of a $w_o$ of about 25 (containing enzyme) with micelles of a $w_o$ of about 5. Thus, the notation 25e+5 was identical with 10e in terms of final enzyme:surfactant:water ratios; the only difference being the method of preparation.

In Case II, AOT (in solid form) was added to enzyme-containing reversed micelles of large $w_o$ to bring down the $w_o$ to the optimum value. Here the AOT (and water) concentrations of the final mixture were higher than in Case I. Case II was used to indirectly examine AOT concentration effects on activity. The notation 25e+A in FIG. 7, for example, was applied to Case II.

Case III was a variant of Cases I and II. AOT was dissolved in isooctane (i.e., micelles of a $w_o = 0$), and the dissolved AOT was then added to enzyme-containing micelles of a large $w_o$. As in Case I, when the AOT concentration was constant, the enzyme concentration decreased upon mixing the two solutions. Hence, as in Case I, the concentration of the enzyme in the solution of a $w_o$ of about 25 was such that the final concentration at a $w_o$ of about 10 was 0.1 mg/ml. The notation for this case in FIG. 7 was 25E+A/I.

Figure 9:
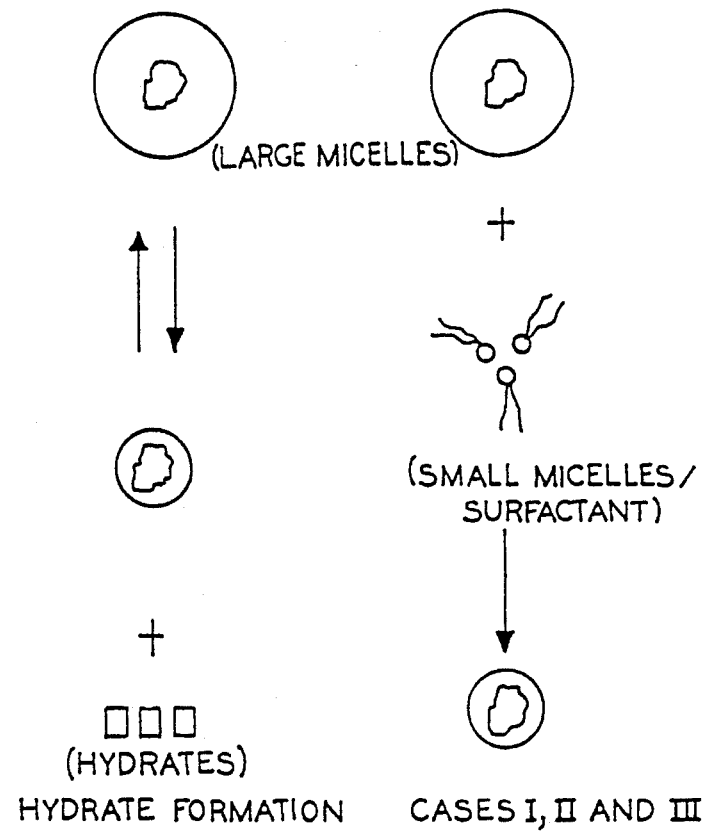
FIG. 9 is a representation of methods of changing $w_o$.

FIG. 9 schematically illustrates the phenomenon behind the different methods of adjusting $w_o$. The hydrate formation method reduces the $w_o$ by reversibly freezing out a portion of the microaqueous phase. In Cases I, II and III the $w_o$ is reduced by mixing small surfactant aggregates with the larger protein-containing microemulsion droplets.

Figure 8:
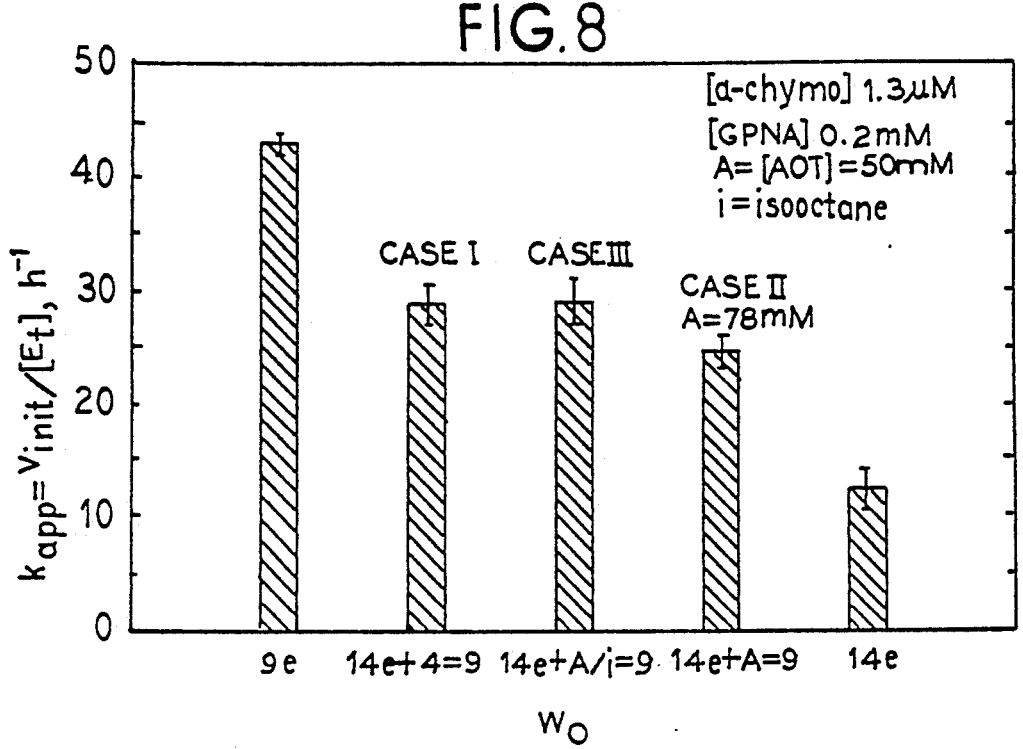
FIG. 8 illustrates alternate methods of changing $w_o$ and effects on α-chymotrypsin activity.

Turning to FIGS. 7 and 8, the final enzyme and substrate concentrations were substantially identical in all cases. The AOT concentration for Case II was higher than the other cases, as shown. It was observed that all methods of $w_o$ reduction to a more optimal level resulted in enhanced activity. To some extent, this reflects the fact that reversed micelles are dynamic entities. During the process of collision, constituent exchange, and reformation of micelles, the encapsulated enzyme was perhaps able to alter conformation to a state dictated by the micelle size. However, enzyme activity was not enhanced to the levels obtained by encapsulating enzyme at the appropriate $w_o$ (10e in FIG. 7 and 9e in FIG. 8), indicating that simultaneous encapsulation and reversed micelle formation results in the most active confirmation.

Figure 10:
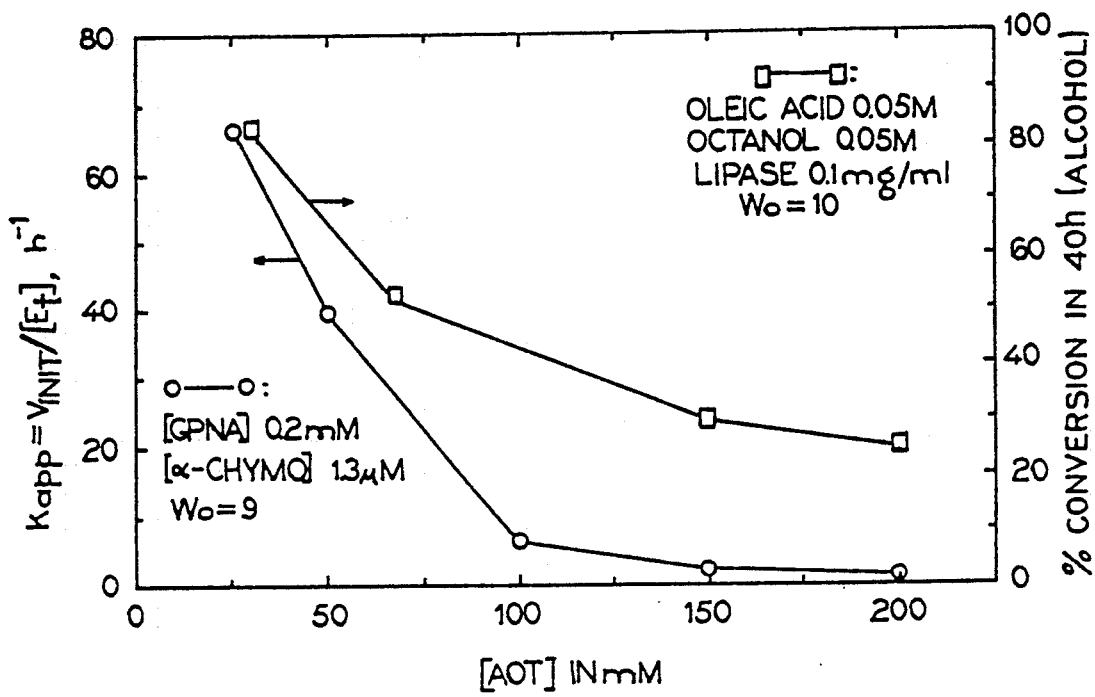
FIG. 10 illustrates enzyme activity inhibition through increased surfactant concentrations (at constant $w_o$)

As shown in FIGS. 7 and 8, with increased surfactant concentrations (Case II in FIGS. 9 and 10), the enzyme activity was least enhanced. The inhibitory effect of the surfactant concentration was clearly shown in FIG. 8, where the $w_o$ was maintained constant.

EXAMPLE II

This example illustrates the use of the membrane mimetic system as an organized medium for synthesizing enzyme-catalyzed polymers in reversed micellar solution using p-ethylphenol monomer as the polymerizable substrate, peroxidase as the catalytic enzyme and a peroxide as the reaction mediating compound.

An enzyme-encapsulated reversed micellar solution was first prepared by the injection method as described in Example I, except that the enzyme was horseradish peroxidase (40,000 molecular weight) obtained from Sigma Chemical Co. The peroxidase was dissolved in the buffer, N-(2-Hydroxyethyl)piperazine-N'-(2-ethanesulfonic acid), hereafter HEPES. A stock solution of 1.25 mM peroxidase in HEPES buffer, at a pH of about 7.5, was prepared and about 0.15 Moles AOT was dissolved in isooctane.

Sufficient enzyme-containing aqueous phase was added to the isooctane-AOT solution to achieve an overall enzyme concentration of about 0.5 mg/ml and a buffer concentration of about 1.5M in the reaction mixture. This resulted in a reversed micellar solution having a $w_o$ (buffer to AOT molar ratio) of about 10. A molar concentration of about 0.15M p-ethylphenol was then added to the reversed micellar solution and dissolved therein. The polymerization reaction was then initiated by adding hydrogen peroxide (30% in water) to provide a molar peroxide concentration of about 0.2M, which is in excess of the monomer concentration. The liquid hydrogen peroxide was added gradually at a controlled rate sufficient to maintain the reaction and avoid deactivating the enzyme.

In another test, hydrogen peroxide as the mediating compound also was generated in situ by a glucose oxidation coupled reaction. In this case, the enzyme glucose oxidase was encapsulated in addition to peroxidase in the reversed micelles. Glucose was then added to produce gluconic acid and hydrogen peroxide. The hydrogen peroxide generated was then used for the polymerization.

The basic reaction mechanism of the addition of a peroxide in the presence of an enzyme forms a transition intermediate state in which the reaction takes place on both positions of the benzyl ring which are ortho to the oxygen substituent of the p-ethylphenol monomer.

The results following hydrate formation showed that enzymatic polymer synthesis in reversed micelles produced spherical particles of micron and submicron size.

Figure 12:
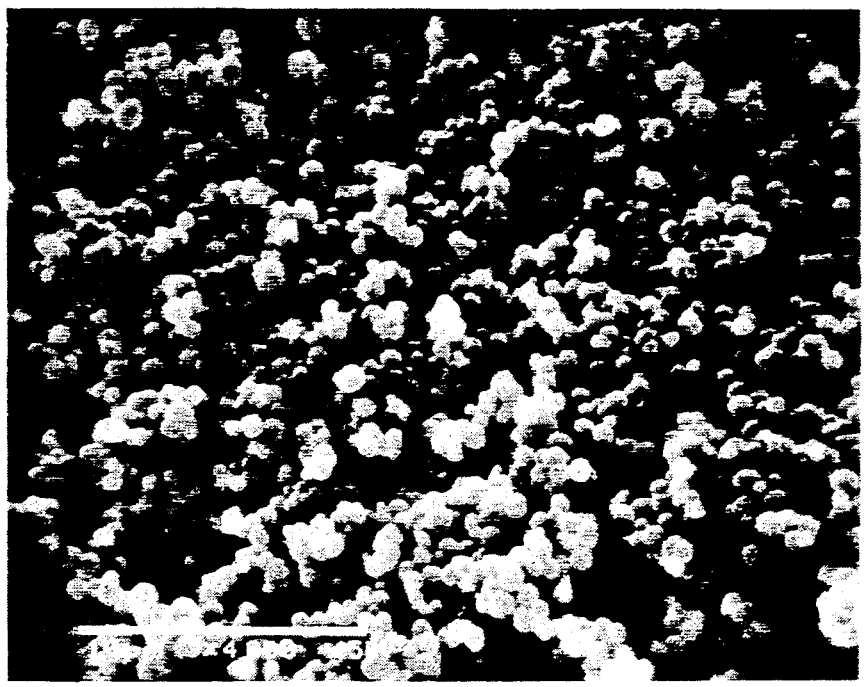
FIG. 12 is an electron micrograph illustrating the spherical particle characteristics of a dried powder of enzymatically synthesized polymer particles.

FIG. 12 is an electron micrograph taken at 4000× magnification of a dried powder of polymer particles of this invention. Reversed micelles were formed from a composition containing about 0.3M AOT, about 0.15M p-ethylphenol buffered to a surfactant molar ratio of about 15:1 with about a 5mg/ml enzyme concentration. Hydrogen peroxide was gradually added in several batches to provide a final concentration of about 0.195M. The polymer particles which formed precipitated out of the solution. The polymer particles were collected by centrifuging and/or filtration. The surfactants were then removed from the polymer by repeated washing with isooctane. The collected particles were then dried to a powder at about 60° C. The electron micrograph of the powder seen in FIG. 12 illustrates the spherical characteristics of the polymer particles.

Similar results were obtained when the procedure was varied by adding enzyme-free HEPES buffer to the isooctane-AOT solution to a buffer concentration of about 1.69M in the solution and then adding an aliquot of the stock enzyme-containing buffer solution to provide an additional buffer concentration of 0.56M for a total buffer 25 concentration of about 2.25M. This procedure produced a reversed micellar solution having a $w_o$ (water to AOT molar ratio) of about 15 and a total enzyme concentration of about 12.5μM.

Other variations in the preparation scheme and the concentration of the components also were made by varying the weight percent basis of the three components, (i) the solvent, isooctane; (ii) the buffer; and (iii) the surfactant, in the reversed micellar-solution between about 0.1 to about 99 weight percent relative to one another.

In one case, the weight percent of the three components was about 25 weight percent buffer, about 25 weight percent surfactant and about 50 weight percent isooctane. In another case, the components were about 3 weight percent surfactant, about 30 weight percent buffer and about 67 weight percent isooctane. The enzyme concentration used in these tests ranged upwards from a minimum of 0.1 mg/ml. The substrate (monomer) concentration varied from a monomer:surfactant concentration of from about 0.1:10 to about 10:1.

Figure 11:
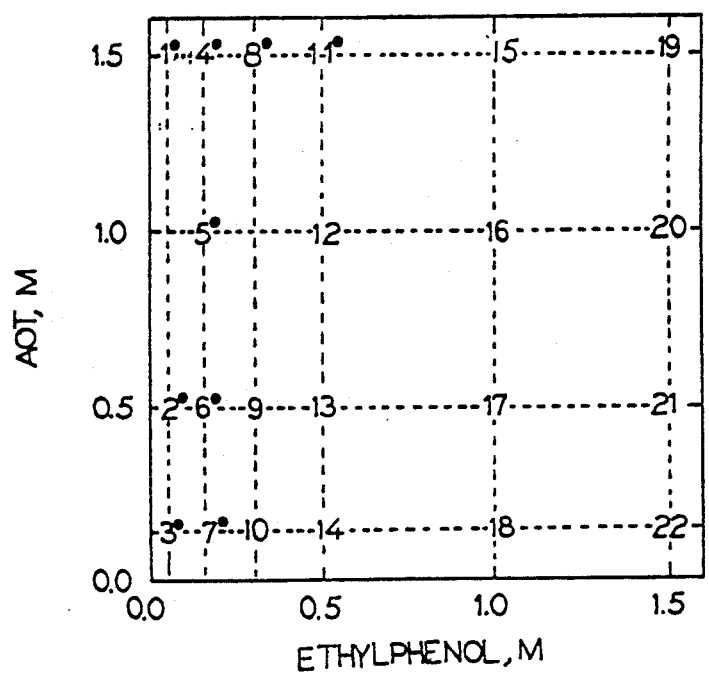
FIG. 11 is a diagram of the effect on the morphology of the polymer particles formed as a function of concentration of AOT to p-ethylphenol.

When the concentration of AOT and isooctane was varied from 0 to about 1.5M relative to one another, it was found that a high AOT surfactant concentration to p-ethylphenol concentration influenced the formation of spherical particles. The results illustrating the effect on the morphology of the polymer particles formed in 22 compositions tested are shown by FIG. 11. The filled circle in FIG. 11 adjacent to the number indicated those compositions where spherical polymer particles were formed having particle sizes ranging from 0.1 μm to 5 μm.

As the AOT surfactant to p-ethylphenol concentration ratio was decreased, the polymer particles had no specific shape and attained irregular morphologies. This is similar to synthesis in bulk monophasic organic solvents (e.g. dioxane and water) which also leads to large particles with irregular shapes.

Thus, by operating in different composition regions of the surfactant-water-isooctane phase diagram, the microstructure of the fluid medium making up the reversed micelles changed shapes. It is believed that polymerization in these various composition regions results in polymer particles that reflect the morphology of the fluid microstructure.

Reversed micelles are characterized by having substantially large interfacial areas. Since monomers, such as phenols and aromatic amines, are themselves amphiphilic, it is believed that the monomeric species align themselves at the oil-water interface with the hydroxyl (or amine groups) directed at the microaqueous core of the micelles resulting in the synthesis of oriented polymers and optimal coupling and chain growth.

While enzymatic polymer synthesis has been illustrated using reversed micelles (water-in-oil microemulsions), it is not limited thereto. Preliminary results using oil-in-water microemulsions for long-chain enzyme-catalyzed polymerization reactions have resulted in enhanced solubility of the growing chain when solvent, such as isooctane, and surfactant are used to prepare the oil-in-water microemulsion.

What is claimed is:

1. A method for controlling the internal reaction medium of a membrane mimetic system, the method comprising the steps of:
   a) preparing a solution of a solvent and a solute to form an admixture containing an internal reaction medium enclosed by a membrane mimetic system; and
   b) reversibly isolating a portion of the solvent within the admixture so as to raise the effective concentration of the solute in the admixture to a level sufficient to cause a change in the concentration of the solute in the internal reaction medium.

2. The method of claim 1 wherein the portion of the solvent is isolated by combining the solvent with a gas capable of forming a hydrate.

3. The method of claim 2 wherein the gas is provided to the admixture under pressure.

4. The method of claim 2 wherein the solvent is water.

5. The method of claim 1 wherein the reaction medium is encapsulated in reversed micelles.

6. The method of claim 1 wherein step (b) is repeated at least once.

7. The method of claim 1 further including the steps of subsequently releasing the isolated portion of the solvent so as to reduce the effective concentration of the solute in the internal reaction medium.

8. The method of claim 1 wherein the internal reaction medium comprises a protein, a denaturant and water.

9. The method of claim 1 wherein the internal reaction medium comprises an enzyme, at least one polymerizable monomer and water.

10. The method of claim 9 wherein the internal reaction medium also includes a liquid hydrocarbon solvent and at least one surfactant.

11. A method for controlling enzymatic polymer synthesis within the internal reaction medium of a membrane mimetic system, the method comprising the steps of:
    a) admixing a first solution comprising at least one enzyme dissolved in aqueous buffer solution with a second solution comprising at least one surfactant dissolved in a liquid hydrocarbon solvent to form a reversed micellar solution;
    b) dissolving at least one substrate capable of being polymerized in the reversed micellar solution to provide an internal reaction medium comprising the foregoing solutes; and
    c) reversibly isolating a portion of the solvent within the reaction medium so as to raise the effective concentration of the solute in the admixture to a level sufficient to cause a change in the concentration of the solute in the reaction medium.

12. The method of claim 11 wherein the at least one enzyme is a catalytic enzyme selected from the group consisting of peroxidase, tyrosinase and laccase.

13. The method of claim 11 wherein the at least one surfactant is selected from the group consisting of anionic, cationic and nonionic surfactants.

14. The method of claim 11 wherein the at least one surfactant is a bis(2-ethylhexyl) sulfosuccinate salt.

15. The method of claim 14 wherein the at least one surfactant is present at a concentration of from at least about 0.01M.

16. The method of claim 11 wherein the solvent is a liquid hydrocarbon.

17. The method of claim 16 wherein the solvent is isooctane.

18. The method of claim 11 wherein the enzyme is present at a concentration of at least about 0.1 mg/ml.

19. The method of claim 11 wherein the substrate is a member of the group consisting of polymerizable monomers having phenolic or aromatic amine groups.

20. The method of claim 11 wherein the monomer:-surfactant ratio ranges from about 0.1:10 to about 10:0.1.

21. The method of claim 20 wherein the monomer is p-ethylphenol and the surfactant is an anionic surfactant.

22. A polymer which can be obtained by the method of claim 11 having a spherical particle size of less than about 5 μm.

23. The method of claim 11, further including the step of adding a reaction mediating compound to the reversed micellar solution in an amount sufficient for initiating polymerization.

24. The method of claim 23 wherein the at least one enzyme is peroxidase and the reaction mediating compound is a source of hydrogen peroxide.

25. The method of claim 23 wherein the reaction mediating compound is generated in situ.

26. The method of claim 25 wherein the reaction mediating compound is hydrogen peroxide and is generated by further including glucose oxidase in the reversed micellar solution and then adding glucose in an amount sufficient for reaction therewith to generate hydrogen peroxide in situ.

* * * * *

UNITED STATES PATENT AND TRADEMARK OFFICE
CERTIFICATE OF CORRECTION

PATENT NO. : 5,324,436
DATED      : June 28, 1994
INVENTOR(S): Vijay T. John, Joseph A. Akkara and David L. Kaplan It is certified that error appears in the above-indentified patent and that said Letters Patent is hereby corrected as shown below:

Col. 3, line 24, change "micelies," to --micelles,--.
Col. 6, line 65, change "(AEROSOL TO," to --(AEROSOL OT,--.
Col. 8, line 12, change "Aerosol-TO/Isooctane" to --Aerosol-OT Isooctane--.
Col. 14, line 61, change "cell. suspended" to --cell suspended--.
Col. 17, line 55, change "$w_o$appeared" to --$w_o$ appeared--.
Col. 18, line 9, change "$w_o$data" to --$w_o$ data--.
Col. 18, line 17, change "$w_o$values" to --$w_o$ values--.
Col. 19, line 28, change "$w_o$(10e" to --$w_o$ (10e--.
Col. 20, line 41, change "buffer 25 concentration" to --buffer concentration--.
Col. 21, Claim 5, line 2, change "micelies." to --micelles.--.

Signed and Sealed this

Sixth Day of December, 1994

Attest:

BRUCE LEHMAN

Attesting Officer    Commissioner of Patents and Trademarks